US008686042B2

(12) United States Patent
Gil et al.

(10) Patent No.: US 8,686,042 B2
(45) Date of Patent: Apr. 1, 2014

(54) GSK-3 INHIBITORS

(75) Inventors: Ana Martinez Gil, Madrid (ES); Miguel Medina Padilla, Madrid (ES); Mercedes Alonso Cascon, Madrid (ES); Ana Fuertes Huerta, Madrid (ES); Maria Luisa Navarro Rico, Madrid (ES); Maria Jose Perez Puerto, Madrid (ES); Ana Castro Morera, Madrid (ES); Ester Martin Aparicio, Moralzarzal-Madrid (ES)

(73) Assignee: Neuropharma, S.A., Madrid (ES)

( * ) Notice: Subject to any disclaimer, the term of this patent is extended or adjusted under 35 U.S.C. 154(b) by 1225 days.

(21) Appl. No.: 11/996,962

(22) PCT Filed: Jul. 28, 2006

(86) PCT No.: PCT/EP2006/007520
§ 371 (c)(1),
(2), (4) Date: Jun. 17, 2008

(87) PCT Pub. No.: WO2007/017145
PCT Pub. Date: Feb. 15, 2007

(65) Prior Publication Data
US 2009/0124686 A1 May 14, 2009

(30) Foreign Application Priority Data
Jul. 29, 2005 (EP) .................................. 05380176

(51) Int. Cl.
A01N 43/30 (2006.01)
A61K 31/36 (2006.01)
A01N 47/28 (2006.01)
A61K 31/17 (2006.01)

(52) U.S. Cl.
USPC ............ 514/595; 514/596; 514/598; 514/464

(58) Field of Classification Search
None
See application file for complete search history.

(56) References Cited

U.S. PATENT DOCUMENTS

| 6,300,346 B1 | 10/2001 | Sperl et al. |
| 2004/0092535 A1 | 5/2004 | Barsanti et al. |
| 2005/0119274 A1 | 6/2005 | Evenou et al. |

FOREIGN PATENT DOCUMENTS

| EP | 0 839 803 A1 | 5/1998 |
| GB | 2 036 555 A | 7/1980 |
| WO | 0006156 A1 | 2/2000 |
| WO | 0229091 A2 | 4/2002 |
| WO | 03004472 A1 | 1/2003 |
| WO | 03004475 A1 | 1/2003 |
| WO | 03004478 A1 | 1/2003 |
| WO | 03089419 A1 | 10/2003 |
| WO | 2005002552 A2 | 1/2005 |

OTHER PUBLICATIONS

Meijer et al. "Pharmacological inhibitors of glycogen synthase kinase 3", TrendsPharm.Sci., 2004, vol. 25, issue 9, pp. 471-480.*
Bhat et al. "Structural Insights and Biological Effects of Glycogen Synthase Kinase 3-specific Inhibitor ARA014418", J.Biol.Chem., 2003, vol. 278, issue 46, pp. 45937-45945.*
Martinez et al. "First Non-ATP Competitive Glycogen Synthase Kinase 3 beta (GSK-3beta) Inhibitors: Thiadiazolidinones (TDZD) as Potential Drugs for the Treatment of Alzheimer's Disease", J.Med. Chem., 2002, vol. 45, pp. 1292-1299.*
Braese et al., J.Comb.Chem., 2000, vol. 2, pp. 710-715.*
Neidle, Cancer Drug Design and Discovery, Elsevier/Academic Press, 2008, pp. 427-431.*
Dragunow, "The adult human brain in preclinical drug development", Nat.Rev.DrugDisc., 2008, vol. 7, pp. 659-666.*
Noorbakhsh et al. "Deciphering complex mechanisms in neurodegenerative diseases: the advent of systems biology", Trends in Neurosciences, 2009, vol. 32, issue 2, pp. 88-100.*
Kramer et al. "Small-Molecule Inhibitors of GSK-3: Structural Insights and Their Application to Alzheimer's Disease Models", Int. J. Alz. Dis., 2012, vol. 2012, Article ID 381029, 32 pages.*
Ashcroft, M., et al., "The selective and inducible activation of endogenous PI 3-kinase in PC12 cells results in efficient NGF-mediated surv . . . ", "Oncogene", 1999, pp. 4586-4597, vol. 18.
Ballin, A., et al., "The Effect of Lithium Chloride on Tumour Appearance and Survival of Melanoma-Bearing Mice", "Br. J. Cancer", 1983, pp. 83-87, vol. 48.
Bienz, M., et al., "Linking Colorectal Cancer to WNT Signaling", "Cell", 2000, pp. 311-320, vol. 103.
Chen, G., et al., "The Mood-Stabilizing Agent Valproate Inhibits the Activity of Glycogen Synthase Kinase-3", "J. Neurochem.", 1999, pp. 1327-1330, vol. 72.

(Continued)

*Primary Examiner* — James D Anderson
*Assistant Examiner* — Stephanie Springer
(74) *Attorney, Agent, or Firm* — Hultquist PLLC; Steven J. Hulquist; Mary B. Grant

(57) ABSTRACT

The invention relates to urea derivatives of formula (I) as inhibitors of glycogen synthase kinase 3β, GSK-3, to processes of preparation of such compounds, to pharmaceutical compositions comprising them, and to their use for the treatment and or prophylaxis of a disease in which GSK-3 is involved, such as Alzheimer's disease or non-insulin dependent diabetes mellitus.

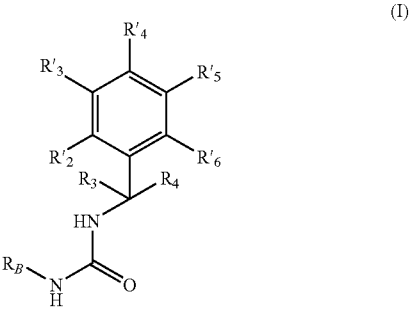

(I)

1 Claim, 3 Drawing Sheets

(56) References Cited

OTHER PUBLICATIONS

Chen, G., et al., "Glycogen synthase kinase 3β (GSK3β) mediates 6-hydroxydopamine-induced neuronal death", "The FASEB Journal", 2004, pp. 1162-1164, vol. 18, No. 10.

Dou, H., et al., "Neuroprotective Activities of Sodium Valproate in a Murine Model of Human Immunodeficiency Virus-1 Encephalitis", "The Journal of Neuroscience", 2003, pp. 9162-9170, vol. 23, No. 27.

Everall, I., et al., "Lithium Ameliorates HIV-gp120-Mediated Neurotoxicity", "Molecular and Cellular Neuroscience", 2002, pp. 493-501, vol. 21.

Ferrer, I., et al., "Current Advances on Different Kinases Involved in Tau Phosphorylation, and Implications in Alzheimer's Disease and Tau . . . ", "Current Alzheimer Research", 2005, pp. 3-18, vol. 2.

Fishman, P., et al., "Evidence for involvement of Wnt signaling pathway in IB-MECA mediated suppression of melanoma cells", "Oncogene", 2002, pp. 4060-4064, vol. 21.

Fujio, Y., et al., "Akt Promotes Survival of Cardiomyocytes In Vitro and Protects Against Ischemia-Reperfusion Injury in Mouse Heart", "Circulation", 2000, pp. 660-667, vol. 101.

Gotoh, J., et al., "Cyclin D1 Over-Expression Correlates With β-Catenin Activation, But Not With H-RAS Mutations, and Phosphorylation . . . ", "Carcinogenesis", 2003, pp. 435-442, vol. 24, No. 3.

Gottesman, I., et al., "The Endophenotype Concept in Psychiatry: Etymology and Strategic Intentions", "Am. J. Psychiatry", 2003, pp. 636-645, vol. 160.

Gould, T., et al., "Signaling networks in the pathophysiology and treatment of mood disorders", "Journal of Psychosomatic Research", 2002, pp. 687-697, vol. 53.

Grimes, C., et al., "The multifaceted roles of glycogen synthase kinase 3β in cellular signaling", "Progress in Neurobiology", 2001, pp. 391-426, vol. 65.

Jope, R., et al., "Lithium and Brain Signal Transduction Systems", "Biochemical Pharmacology", 1994, pp. 429-441, vol. 47, No. 3.

Kaytor, M., et al., "The GSK3β Signaling Cascade and Neurodegenerative Disease", "Current Opinion in Neurobiology", 2002, pp. 275-278, vol. 12.

Kim, A., et al., "Valproate protects cells from ER stress-induced lipid accumulation and apoptosis by inhibiting glycogen synthase . . . ", "Journal of Cell Science", 2005, pp. 89-99, vol. 118.

Li, M., et al., "Cyclic AMP Promotes Neuronal Survival by Phosphorylation of Glycogen Synthase Kinase 3β", "Molecular and Cellular Biology", 2000, pp. 9356-9363, vol. 20, No. 24.

Linseman, D., et al., "A Myocyte Enhancer Factor 2D (MEF2D) Kinase Activated During Neuronal Apoptosis Is a Novel Target Inhibited by Lithium", "Journal of Neurochemistry", 2003, pp. 1488-1499, vol. 85.

Loberg, R., et al., "Enhanced Glycogen Synthase Kinase-3β Activity Mediates Hypoxia-induced Apoptosis of Vascular Smooth Muscle Cells . . . ", "The Journal of Biological Chemistry", 2002, pp. 41667-41673, vol. 277, No. 44.

Maggirwar, S., et al., "HIV-1 TAT-Mediated Activation of Glycogen Synthase Kinase-3β Contributes to TAT-Mediated Neurotoxicity", "J. Neurochem.", 1999, pp. 578-586, vol. 73.

Mattson, M., "Apoptosis in Neurodegenerative Disorders", "Nature Reviews", 2000, pp. 120-129, vol. 1.

Mazor, M., et al., "Inhibition of glycogen synthase kinase-3 represses androgen receptor activity and prostate cancer cell growth", "Oncogene", 2004, pp. 7882-7892, vol. 23.

Meier, R., et al., "Inactivation and Dephosphorylation of Protein Kinase Bα (PKBα) Promoted by Hyperosmotic Stress", "The EMBO Journal", 1998, pp. 7294-7303, vol. 17, No. 24.

Nadri, C., et al., "Glycogen synthase kinase (GSK)-3β levels and activity in a neurodevelopmental rat model of schizophrenia", "Developmental Brain Research", 2003, pp. 33-37, vol. 141.

Ougolkov, A., et al., "Glycogen Synthase Kinase-3β Participates in Nuclear Factor κB-Mediated Gene Transcription and Cell Surviva . . . ", "Cancer Res.", 2005, pp. 2076-2081, vol. 65, No. 6.

Pap, M., et al., "Role of Glycogen Synthase Kinase-3 in the Phosphatidylinositol 3-Kinase/Akt Cell Survival Pathway", "The Journal of Biological Chemistry", 1998, pp. 19929-19932, vol. 273, No. 32.

Pap, M., et al., "Role of Translation Initiation Factor 2B in Control of Cell Survival by the Phosphatidylinositol 3-Kinase/Akt/Glycogen . . . ", "Molecular and Cellular Biology", 2002, pp. 578-586, vol. 22, No. 2.

Rask, K., et al., "WNT-Signalling Pathway in Ovarian Epithelial Tumours: Increased Expression of β-Catenin and GSK3β", "British Journal of Cancer", 2003, pp. 1298-1304, vol. 89.

Song, L., et al., "Central Role of Glycogen Synthase Kinase-3β in Endoplasmic Reticulum Stress-induced Caspase-3 Activation", "The Journal of Biological Chemistry", 2002, pp. 44701-44708, vol. 277, No. 47.

Sutherland, C., et al., "Inactivation of Glycogen Synthase Kinase-3β by Phosphorylation: New Kinase Connections in Insulin and Growth-Fact . . . ", "Biochem J.", 1993, pp. 15-19, vol. 296.

Tong, N., et al., "Activation of Glycogen Synthase Kinase 3 Beta (GSK-3β) by Platelet Activating Factor Mediates Migration and Cell . . . ", "European Journal of Neuroscience", 2001, pp. 1913-1922, vol. 13.

* cited by examiner

1H-NMR

13C-NMR

1H-NMR

13C-NMR

GSK-3 INHIBITORS

CROSS REFERENCE TO RELATED APPLICATIONS

This application is filed under the provisions of 35 USC 371 based on International Application PCT/EP2006/007520, claiming priority of European Patent Application No. 05380176.7 filed Jul. 29, 2005. The disclosures of such international patent application and European patent application are hereby incorporated herein by reference, in their respective entireties, for all purposes.

FIELD OF THE INVENTION

The present invention relates to enzyme inhibitors, and more particularly to urea derivatives as inhibitors of glycogen synthase kinase 3β, GSK-3, to processes of preparation of such compounds, to pharmaceutical compositions comprising them, and to their use for the treatment and or prophylaxis of a disease in which GSK-3 is involved, such as Alzheimer's disease or non-insulin dependent diabetes mellitus.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases. Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes (Coghlan et al., *Chemistry & Biology*, 7, 793-803 (2000); Kim and Kimmel, *Curr. Opinion Genetics Dev.*, 10, 508-514 (2000)). The threonine/serine kinase glycogen synthase kinase-3 (GSK-3) fulfills a pivotal role in various receptor-linked signalling pathways (Doble, B W, Woodgett, J R *J. Cell Sci.* 2003, 116:1175-1186). Dysregulation within these pathways is considered a crucial event in the development of several prevalent human disorders, such as type II diabetes (Kaidanovich O, Eldar-Finkelman H, *Expert Opin. Ther. Targets,* 2002, 6:555-561), Alzheimer's disease (Grimes C A, Jope R S, *Prog. Neurobiol.* 2001, 65:391-426), CNS disorders such as manic depressive disorder and neurodegenerative diseases, and chronic inflammatory disorders (Hoeflich K P, Luo J, Rubie E A, Tsao M S, Jin O, Woodgett J, *Nature* 2000, 406:86-90). These diseases may be caused by, or result in, the abnormal operation of certain cell signalling pathways in which GSK-3 plays a role.

GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor eIF2B, as well as ATP citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

Currently, inhibition of GSK-3 may represent a viable strategy to develop novel medicinal entities for the treatment of such unmet diseases (Martinez A, Castro A, Dorronsoro 1, Alonso M, *Med. Res. Rev.,* 2002, 22:373-384) through insulin mimicry, tau dephosphorylation and amyloid processing, or transcriptional modulation respectively.

In the State of the Art, some compounds containing an urea group have already been described as having GSK-3 inhibitory properties. This is the case, for example, of publications WO03/004472, WO03/004475 and WO03/089419. These publications refer each one to a very broad number of compounds defined by a Markush structure, said structure being big and complex, this circumstance making their preparation more complicated and increasing the probability of reactivity of the compounds. Particularly, these compounds pertain to structural subgroups such as substituted thiazole compounds and heterocyclic amines. These compounds may contain, among many other groups, an urea functional group. These compounds are generally said to have inhibitory effects on GSK-3, and thus potential activity in the treatment and prevention of a series of diseases related to GSK-3, such as dementias, diabetes and mood disorders. Nevertheless, no results regarding GSK-3 inhibition for any particular compounds are included in any of the above-mentioned publications; that is, neither for those comprising an urea functional group any results really proving any activity of these urea derivatives are shown.

On the other hand, Publication WO03/004478 and article "Structural Insights and Biological Effects of GSK-3 specific Inhibitor AR-A014418", J. Biol. Chem., 278 (46), 2003 deal with one particular urea, 4-(4-methoxybenzyl)-N'-(5-nitro-1,3-thiazol-2-yl)urea; this urea indeed has a much smaller and simpler structure than the above mentioned ureas. It is described as having GSK-3 inhibitory properties, and thus as having potential activity for treating and/or preventing numerous conditions associated with glycogen synthase kinase 3. Nevertheless, it is not clear whether the GSK-3 inhibitory effect is due to the urea itself or to the nitro-thiazole, as heterocyclic compounds have been described as having GSK-3 inhibitory properties, see for example above-mentioned WO03/089419.

Some other ureas have been described in relation to the treatment of neurological disorders, but in relation with completely different methods of action, for example WO00/06156, wherein the disclosed ureas are described to be potentiators of glutamate receptor function.

There is therefore still a need to find good GSK-3 inhibitors, being both effective and selective, and having good "drugability" properties, i.e. good pharmaceutical properties related to administration, distribution, metabolism and excretion. An additional advantage would be to find compounds with simple, stable structures, being easy to be prepared by ordinary proceedings known to the skilled person.

DESCRIPTION OF THE INVENTION

It has now been found that a group of stable and small urea derivatives shows inhibitory effects on GSK-3 enzyme.

Use of a compound of formula (I)

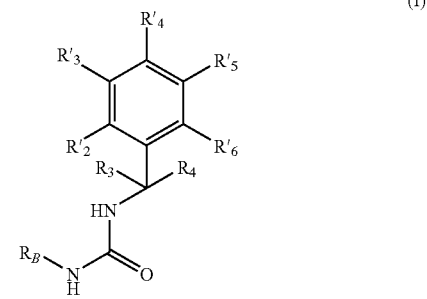

(I)

or any pharmaceutically acceptable salt, prodrug or solvate thereof, wherein:

$R_B$ is selected from substituted or unsubstituted alkyl, substituted or unsubstituted cycloalkyl, substituted or unsubstituted aryl wherein aryl is selected from the group of phenyl, naphthyl, fenanthryl and anthracyl, substituted or unsubstituted aralkyl wherein aralkyl is benzyl, heterocycle selected from the group of azepines, benzimidazole, benzothiazole, furan, imidazole, indole, piperidine, piperazine, purine, thiadiazole, tetrahydrofuran, benzodioxol, thiophene, benzofurane, indazole, quinazoline, pyridazine, pyrimidine, pyrazine, pyridine, isoxazole, pyrrole, pyrane, —$OR_5$, and —$S(O)_t$—$R_5$, wherein $R_B$ comprises from 8 to 15 atoms selected from C, O, N, and S, with the proviso that $R_B$ is not a heterocycle substituted by a heterocycle, $R_3$, $R_4$, $R'_2$, $R'_3$, $R'_4$, $R'_5$ y $R'_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocycle, —C(=O)$R_7$, —C(=O)O$R_8$, —C(=O)N$R_9R_{10}$, —C=N$R_{11}$, —CN, —O$R_{12}$, —OC(=O)$R_{13}$, —S(O)$_n$—$R_{14}$, —N$R_{15}R_{16}$, —N$R_{17}$C(=O)$R_{18}$, —NO, —N=C$R_{19}R_{20}$ or halogen, wherein $R_3$ and $R_4$ together may form a =O group, and wherein any pair of $R_3$, $R'_2$, $R_3$, $R_6$, $R_4$, $R'_2$, $R_4$, $R'_6$, $R'_2R'_3$, $R'_3R'_4$, $R'_4R'_5$, $R'_5R'_6$, $R_{15}R_{16}$, $R_{17}R_{18}$ or $R_{19}R_{20}$ may form together a cyclic substituent; t is 0, 1, 2, 3

$R^5$ is selected from hydrogen, alkyl, aryl and heterocycle;

$R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R^{19}$ and $R_{20}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocycle, substituted or unsubstituted alkoxy, substituted or unsubstituted ariloxy, halogen, in the manufacture of a medicament for the treatment and/or prevention of a GSK-3 mediated disease or condition wherein the disease or condition is selected from the group of diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders, promotion of functional recovery post stroke, cerebral bleeding such as due to solitary cerebral amyloid angiopathy, hair loss, obesity, hypertension, polycystic ovary syndrome, syndrome X, ischaemia, brain injury, traumatic brain injury, cancer, leukopenia, Down's syndrome, Lewy body disease, inflammation, chronic inflammatory diseases, cancer and hyperproliferative diseases as hyperplasias and immunodeficiency.

Preferred compounds are those wherein $R_B$ comprises an aromatic group.

In a particular embodiment, $R_B$ has at least 10 aromatic carbon atoms.

In an additional aspect, the invention is related to a compound of formula

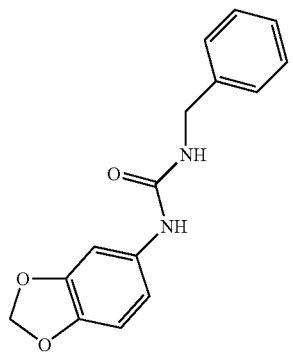 [SMILES: O=C(NCc1ccccc1)Nc1ccc2c(c1)OCO2]

In another aspect, the invention is related to a pharmaceutical composition which comprises a compound of formula (I) as described above or a pharmaceutically acceptable salt, prodrug or solvate thereof and a pharmaceutically acceptable carrier, adjuvant or vehicle.

Preferably, the disease or condition mediated by GSK-3 is selected from Alzheimer's disease, type II diabetes, depression and brain injury.

According to another aspect, the compounds of formula (I) as defined above may be used as reactives for biological assays, preferably as a reactive for GSK-3 inhibition.

DETAILED DESCRIPTION OF THE INVENTION

Figure 1:
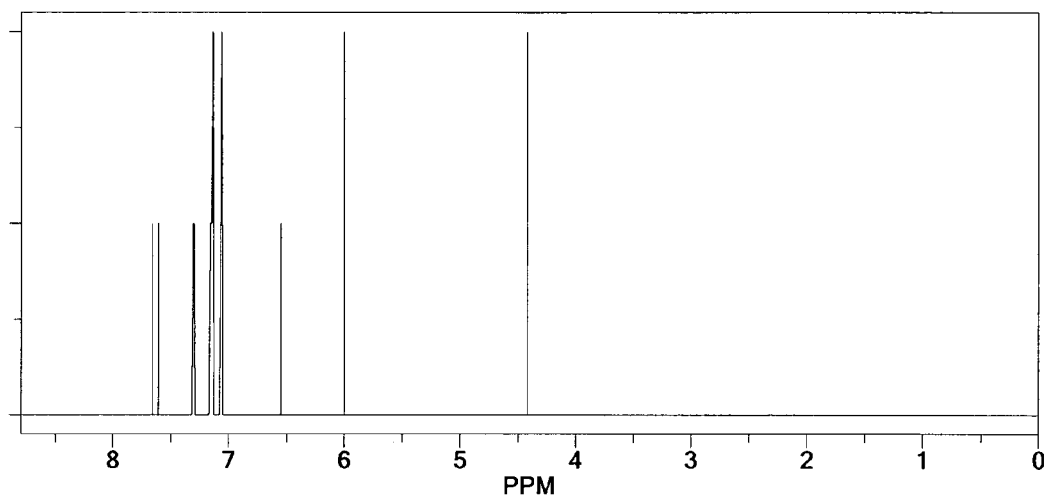
FIG. 1.—Represents the 1H-NMR and 13C-NMR spectra of 1-Benzyl-3-naphtalen-1-yl-urea FIG. 2.—Represents the 1H-NMR and 13C-NMR spectra of 1-Benzo[1,3]dioxol-5-yl-3-benzyl-urea FIG. 3.—Diagram showing GSK-3 activity of 1-Benzyl-3-naphtalen-1-yl-urea measured at different concentrations. The results are reflected in comparison with the control.
Figure 1:
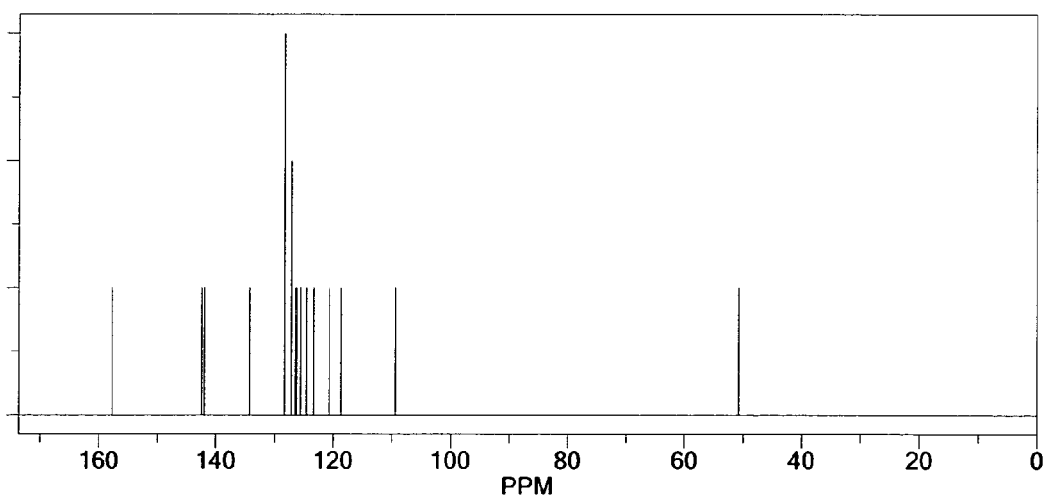

The urea derivatives of formula (I) according to the present invention are chemical entities which surprisingly have shown good inhibitory effects on GSK-3 enzyme, together with a good stability and low toxicity.

As indicated above, in a first aspect the present invention is related to the use of compounds of formula (I) or any pharmaceutically acceptable salt, prodrug or solvate thereof, in the preparation of a medicament for the treatment of a disease or condition mediated by GSK-3. Preferably, $R_B$ comprises an aromatic group and even more preferably $R_B$ has at least 10 aromatic carbon atoms.

In a preferred embodiment, the compound of formula (I) has an aromatic group which is directly linked to the N atom of the urea group.

According to another particular embodiment, $R_B$ is a substituted or unsubstituted naphtyl group, preferably an unsubstituted alpha-naphtyl group.

Preferably, $R_B$ is selected from:

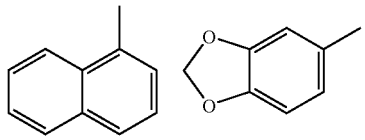

In a particular embodiment, $R_3$ and $R_4$ are H.

In another particular embodiment, $R'_2$, $R'_3$, $R'_4$, $R'_5$ and $R'_6$ are independently selected from hydrogen, substituted or unsubstituted alkyl, —C(=O)R$_7$, —C(=O)OR$_8$, —OR$_{12}$, —NR$_{15}$R$_{16}$, or halogen, wherein $R_7$, $R_8$, $R_{12}$, $R_{15}$ and $R_{16}$ are defined as above.

Preferably, $R'_2$, $R'_3$, $R'_4$, $R'_5$ and $R'_6$ are H.

Two preferred compounds of formula (I) are:

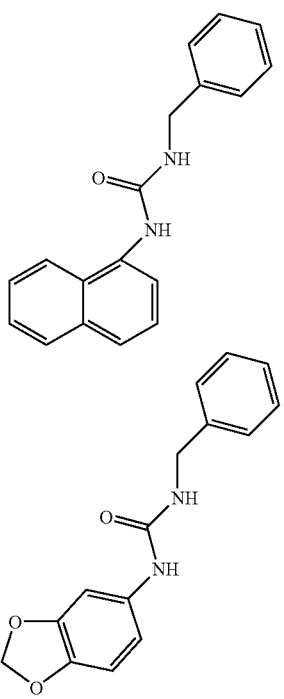

Within the present invention, the expression "GSK-3 mediated disease or condition" means any disease or other deleterious condition or state in which GSK-3 is known to play a role. This disease or condition may be, but is not limited to, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders, promotion of functional recovery post stroke, cerebral bleeding such as due to solitary cerebral amyloid angiopathy, hair loss, obesity, hypertension, polycystic ovary syndrome, syndrome X, ischaemia, brain injury, traumatic brain injury, cancer, leukopenia, Down's syndrome, Lewy body disease, inflammation, chronic inflammatory diseases, cancer and hyperproliferative diseases as hyperplasias and immunodeficiency.

Preferably, the GSK-3 mediated disease or condition is either Alzheimer's Disease, type II diabetes, depression or brain injury.

According to further aspects of the invention, it is related to a compound of formula

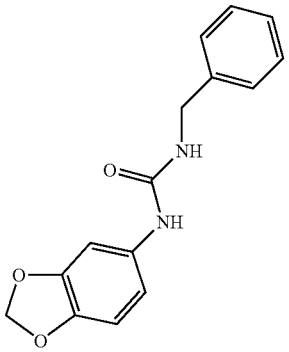 [SMILES: O=C(NCc1ccccc1)Nc1ccc2c(c1)OCO2]

and to its use as a medicament.

Another aspect of the present invention is a pharmaceutical composition comprising a compound as defined above, or any pharmaceutically acceptable salt, prodrug or solvate thereof, and a pharmaceutically acceptable carrier adjuvant or vehicle; preferably, said pharmaceutical composition is for oral administration. Preferred diseases or conditions which may be treated with this pharmaceutical composition may be, but are not limited to, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders, promotion of functional recovery post stroke, cerebral bleeding such as due to solitary cerebral amyloid angiopathy, hair loss, obesity, hypertension, polycystic ovary syndrome, syndrome X, ischaemia, brain injury, traumatic brain injury, cancer, leukopenia, Down's syndrome, Lewy body disease, inflammations, chronic inflammatory diseases, cancer and hyperproliferative diseases as hyperplasias and immunodeficiency.

Another aspect of this invention relates to a method of treating or preventing an GSK-3 mediated disease or condition with a GSK-3 inhibitor, which method comprises administering to a patient in need of such a treatment a therapeutically effective amount of a compound of formula (I) as defined above or a pharmaceutical composition thereof.

In another aspect the invention relates to inhibiting GSK-3 activity in a biological sample with the compounds of formula (I), which method comprises contacting the biological sample with a GSK-3 inhibitor of formula (I). The term "biological sample", as used herein, includes, without limitation, cell cultures or extracts thereof, preparations of an enzyme suitable for in vitro assay; biopsied material obtained from a mammal or extracts thereof; and blood, saliva, urine, feces, semen, tears, or other body fluids or extracts thereof. Thus, in one aspect the invention is directed to the use of compounds of formula I as reactives for biological assays, in particular as a reactive for GSK-3 inhibition.

In the above definition of compounds of formula (I) the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as halo, hydroxy, alkoxy, carboxy, cyano, carbonyl, acyl, alkoxycarbonyl, amino, nitro, mercapto and alkylthio.

"Alkoxy" refers to a radical of the formula —$OR_a$ wherein $R_a$ is an alkyl radical as defined above, e.g., methoxy, ethoxy, propoxy, etc.

"Alkoxycarbonyl" refers to a radical of the formula —C(O)$OR_a$ where $R_a$ is an alkyl radical as defined above, e.g., methoxycarbonyl, ethoxycarbonyl, propoxycarbonyl, etc.

"Alkylthio" refers to a radical of the formula —$SR_a$ where $R_a$ is an alkyl radical as defined above, e.g., methylthio, ethylthio, propylthio, etc.

"Amino" refers to a radical of the formula —$NH_2$, —$NHR_a$ or —$NR_aR_b$, wherein $R_a$ and $R_b$ are independently a radical alkyl as defined above.

"Aryl" refers to a phenyl, naphthyl, indenyl, fenanthryl or anthracyl radical, preferably phenyl or naphthyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Acyl" refers to a radical of the formula —C(O)—$R_c$ and —C(O)—$R_d$ where $R_c$ is an alkyl radical as defined above and $R_d$ is an aryl radical as defined above, e.g., acetyl, propionyl, benzoyl, and the like.

"Aroylalkyl" refers to an alkyl group substituted with —$R_a$—C(O)—$R_d$, wherein $R_a$ is an alkyl radical as defined above and $R_d$ is a radical aryl as defined above. Preferred examples include benzoylmethyl.

"Carboxy" refers to a radical of the formula —C(O)OH.

"Cycloalkyl" refers to a stable 3- to 10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more such as alkyl, halo, hydroxy, amino, cyano, nitro, alkoxy, carboxy and alkoxycarbonyl.

"Halo" refers to bromo, chloro, iodo or fluoro.

"Heterocycle" refers to a heterocyclyl radical. The heterocycle refers to a stable 3- to 15 membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, thiadiazole, tetrahydrofuran, benzodioxol, thiophene, benzofurane, indazole, quinazoline, pyridazine, pyrimidine, pyrazine, pyridine, isoxazole, pyrrole, pyrazole, pyrane.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; unsubstituted cycloalkyl, wherein cycloalkyl is as it was described above; unsubstituted aryl, wherein cycloalkyl is as it was described above, particularly phenyl or naphthyl; and aralkyl such as benzyl. Unless otherwise indicated, an optionally substituted group may have a substituent at each substitutable position of the group, and each substitution is independent of the other.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, derivatives, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drugdesign and Discovery" Taylor & Francis (April 2002).

The compounds of the invention may be in crystalline form either as free compounds or as solvates (e.g. hydrates) and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds of formula (I) defined above can be obtained by available synthetic procedures, for example by reacting:

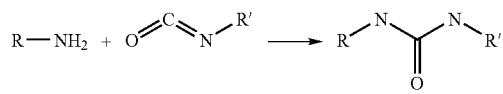

in a suitable solvent, such as N,N-dimethylformamide, dimethyl sulfoxide, dioxane, dichloromethane or tetrahydrofuran, at a temperature within the range of +20 to +150° C.

One preferred pharmaceutically acceptable form is the crystalline form, including such form in a pharmaceutical composition. In the case of salts and solvates the additional ionic and solvent moieties must also be non-toxic. The compounds of the invention may present different polymorphic forms, it is intended that the invention encompasses all such forms.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form. Suitable dose forms for oral administration may be tablets and capsules and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of many of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

In the following, the present invention is further illustrated by examples. They should in no case be interpreted as a limitation of the scope of the invention as defined in the claims.

EXAMPLES

Preparation of Compounds of Formula II

The compounds of formula II according to the present invention where prepared by reacting a convenient isocyanate with a convenient amine in order to obtain the corresponding urea, as described above.

Example 1

Preparation of 1-Benzyl-3-naphthalen-1-yl-urea 0.44 ml (4 mmol) benzylamine are reacted with 0.58 ml (4 mmol) 2-Isocyanato-naphthalene in dichloromethane at room temperature during night:

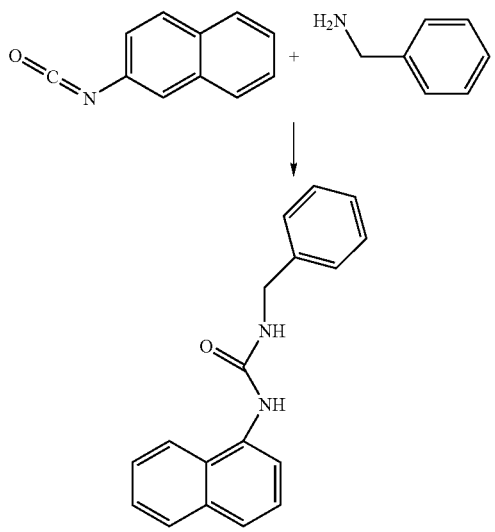

The resulting white precipitate is filtered and washed with diethylether. 1.18 gr of a white powder with a molecular weight of 276 are obtained. Corresponding 1H-NMR and 13C-NMR spectra are indicated in FIG. 1. They show the white compound to be 1-benzyl-3-naphthalen-1-yl-urea.

Example 2

Preparation of 1-Benzol[1,3]-dioxol-5-yl-3-benzyl-urea 0.44 ml (4 mmol) benzylamine are reacted with 654.5 mg (4 mmol) 5-isocyanato-benzo[1,3]dioxole in dichloromethane at room temperature during night:

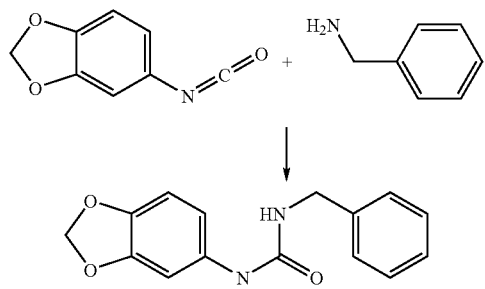

Figure 2:
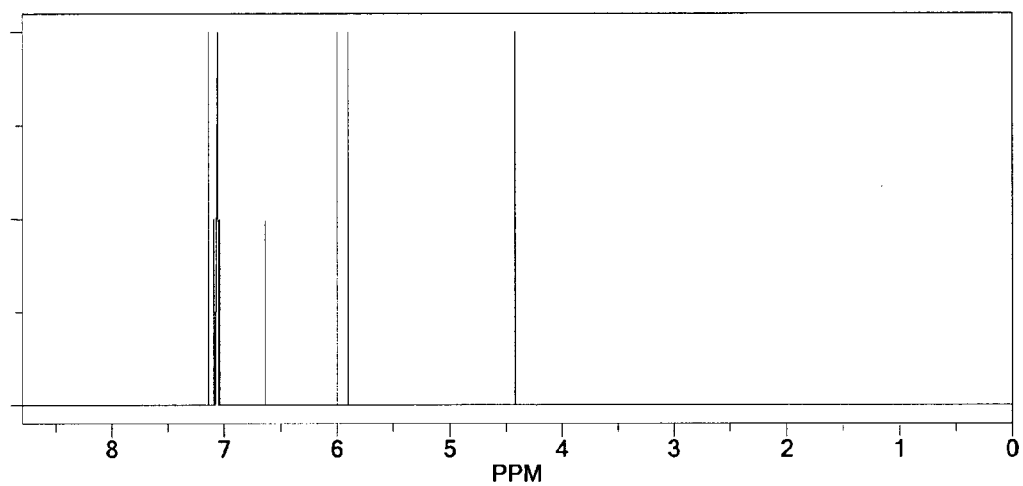
Figure 2:
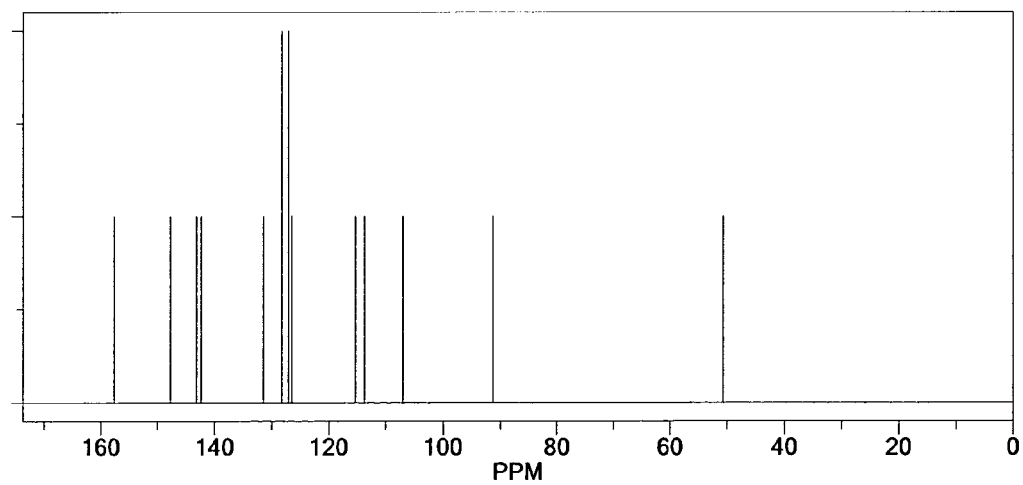

The resulting white precipitate is filtered and washed with diethylether. 1 gr of a white powder with a molecular weight of 276 is obtained. Corresponding 1H-NMR and 13C-NMR spectra are shown in FIG. 2. They show the white compound to be 1-benzyl-3-naphthalen-1-yl-urea.

Biological Methods
GSK-3β Inhibition

The GSK-3β activity was determined by incubation of a mixture of recombinant human GSK-3 enzyme, a phosphate source and GSK-3 substrate in the presence and in the absence of the corresponding test compound, and by measuring the GSK-3 activity of this mixture.

Recombinant human glycogen synthase kinase 3β was assayed in MOPS 8 mM pH 7.3, EDTA 0.2 mM, $MgCl_2$ 10 mM and sodium orthovanadate 0.25 mM in the presence of 62.5 μM of Phospho-Glycogen Synthase Peptide-2 (GS-2), 0.5 μCi γ-$^{33}$P-ATP and unlabelled ATP at a final concentration of 12.5 μM. The final assay volume was 20 μl. After incubation for 30 minutes at 30° C., 15 μl aliquots were spotted onto P81 phosphocellulose papers. Filters were washed four times for at least 10 minutes each and counted with 1.5 ml of scintillation cocktail in a scintillation counter.

Figure 3:
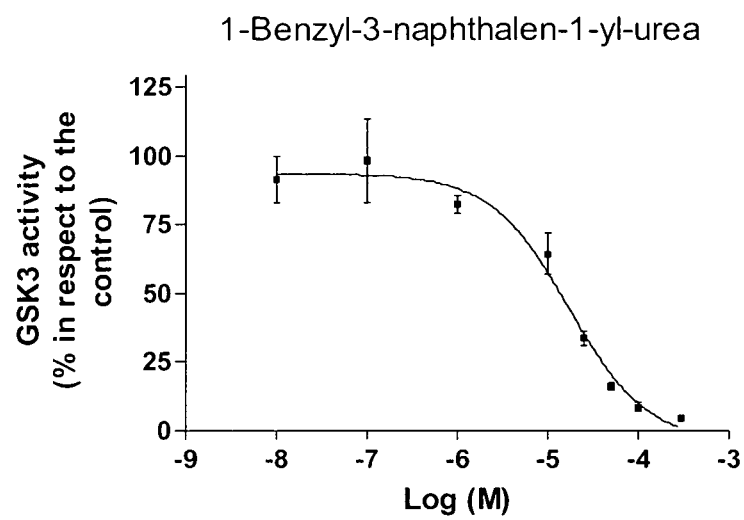
Figure 4:
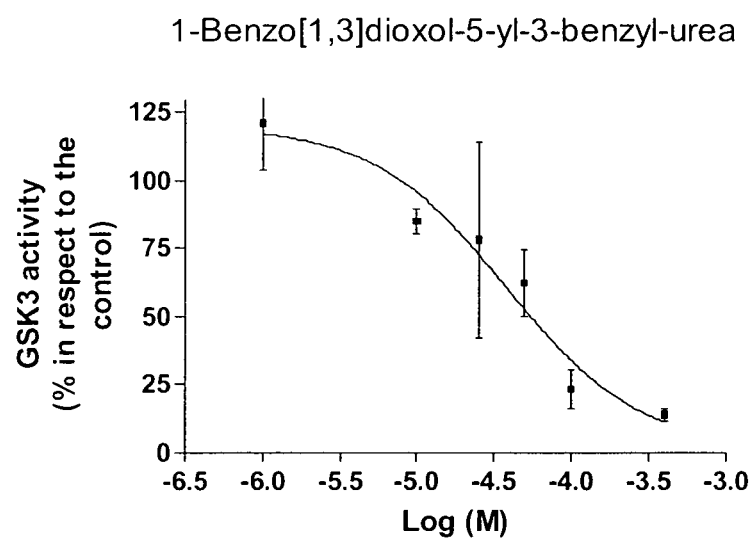
FIG. 4.—Diagram showing GSK-3 activity of 1-Benzo[1,3]dioxol-5-yl-3-benzyl-urea measured at different concentrations. The results are reflected in comparison with the control.

The values for GSK-3 activity in the presence of the compounds according to the present invention were measured at different concentrations; the results, reflected in comparison with the control, are shown in FIGS. 3 and 4.

The compounds' $IC_{50}$ values were calculated analyzing inhibition curves by non-linear regression using GraphPad Prism. The $IC_{50}$ (concentration at which 50% of enzyme inhibition is shown) values are gathered in table 1:

TABLE 1

| Compound | IC50 |
|---|---|
| 1-Benzyl-3-naphthalen-1-yl-urea | 17.1 |
| 1-Benzo[1,3]dioxol-5-yl-3-benzyl-urea | 38.4 |

The invention claimed is:
1. A method of treating Alzheimer's disease, which method comprises administering to a patient in need of such a treatment a therapeutically effective amount of a compound selected from

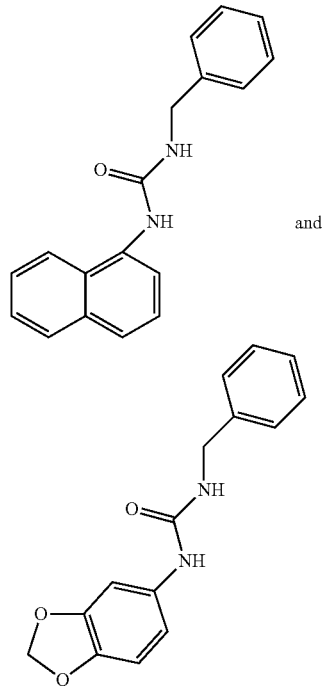

or a pharmaceutically acceptable salt thereof or a pharmaceutical composition comprising said compound.

* * * * *

UNITED STATES PATENT AND TRADEMARK OFFICE
CERTIFICATE OF CORRECTION

PATENT NO. : 8,686,042 B2  
APPLICATION NO. : 11/996962  
DATED : April 1, 2014  
INVENTOR(S) : Ana Martinez Gil Page 1 of 1

It is certified that error appears in the above-identified patent and that said Letters Patent is hereby corrected as shown below:

On the title page of the patent, Item (73) the assignee "Neuropharma, S.A." should be
-- Noscira, S.A. --

Signed and Sealed this
Eighth Day of July, 2014

Michelle K. Lee
*Deputy Director of the United States Patent and Trademark Office*